(12) United States Patent
Tsujimura et al.

(10) Patent No.: US 7,827,874 B2
(45) Date of Patent: Nov. 9, 2010

(54) SAMPLE TREATMENT SYSTEM

(75) Inventors: Naoto Tsujimura, Hitachinaka (JP);
Nobuo Suzuki, Hitachinaka (JP);
Shigeru Yano, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 608 days.

(21) Appl. No.: 11/839,858

(22) Filed: Aug. 16, 2007

(65) Prior Publication Data

US 2008/0047369 A1    Feb. 28, 2008

(30) Foreign Application Priority Data

Aug. 22, 2006    (JP) .............................. 2006-225336

(51) Int. Cl.
*G01M 19/00*    (2006.01)
(52) U.S. Cl. ..................................... 73/865.8
(58) Field of Classification Search ........................ None
See application file for complete search history.

(56) References Cited

U.S. PATENT DOCUMENTS

2006/0014295 A1*   1/2006   Ziegler ....................... 436/164

FOREIGN PATENT DOCUMENTS

| EP | 467302 | 1/1992 |
|---|---|---|
| EP | 869346 | 10/1998 |
| EP | 979998 | 6/2000 |
| EP | 1295843 | 3/2003 |
| EP | 1659090 | 5/2006 |
| JP | 3032159 | 2/2000 |
| WO | WO99/28724 | 6/1999 |

* cited by examiner

*Primary Examiner*—Robert R Raevis
(74) *Attorney, Agent, or Firm*—Mattingly & Malur, P.C.

(57) ABSTRACT

According to the present invention, a sample treatment system is capable of successfully detecting the shape of a stopper of a stopper-equipped sample vessel. A sample treatment system comprises: a sample rack for supporting a stopper-equipped sample vessel in which collected samples are stored; a transfer line for transferring the sample rack; a pretreatment unit that is lined up along the transfer line, and that performs various kinds of pretreatment; and a control unit for controlling the operation of the transfer line and that of the pretreatment unit; wherein the pretreatment unit includes a sample rack supplying unit, a centrifugal separation unit, a stopper opening unit, a dispensing unit, a stopper closing unit, a classification unit, and a sample storing unit, the sample treatment system further comprising shape detection means for detecting the shape of the stopper.

8 Claims, 3 Drawing Sheets

SAMPLE TREATMENT SYSTEM

BACKGROUND OF THE INVENTION

1. Field of the Invention

The present invention relates to a sample treatment system for automating the sample detection used in the clinical laboratory field.

2. Description of the Related Art

In a conventional sample treatment system, the number of stopper shapes of stopper-equipped sample vessels, which can be set in a sample supplying unit included in the system in question, is limited to one. In other words, the conventional sample treatment system cannot cope with a case where there are plural stopper shapes with the limited exception of some similar shapes.

For this reason, at the time of installing the sample treatment system, a user is required to select a stopper-equipped sample vessel to be used from among those specified by a manufacturer. Therefore, it is not always possible to use a stopper-equipped sample vessel which is desired by the user.

In addition, for example, in an inspection center that collects sample vessels entrusted by a plurality of hospitals, and that performs treatment of the sample vessels, a required workload is not small. For example, a large workload is required for moving samples to a sample vessel that can be used in the sample treatment system.

SUMMARY OF THE INVENTION

A sample analysis system disclosed in Japanese Patent No. 3032159 is provided with a plurality of sensors at identification positions of a sample vessel identification unit, the plurality of sensors being located in parallel with a sample vessel. The height of the sample vessel is detected by combinations of whether or not the sample vessel is detected at each position.

It is difficult to identify the shape of a stopper by this identification method for identifying a sample vessel. If a stopper-equipped sample vessel whose shape largely differs is used in the same sample treatment system, it is not possible to avoid a risk that false detection will cause a malfunction at the time of treatment by the pretreatment unit.

The present invention has been made taking the above-described problems into consideration. An object of the present invention is to provide a sample treatment system that is capable of successfully detecting the shape of a stopper of a stopper-equipped sample vessel.

According to one aspect of the present invention, there is provided a sample treatment system comprising: a sample rack for supporting a stopper-equipped sample vessel in which collected samples are stored; a transfer line for transferring the sample rack; a pretreatment unit that is lined up along the transfer line, and that performs various kinds of pretreatment; and a control unit for controlling the operation of the transfer line and that of the pretreatment unit, wherein the pretreatment unit includes a sample rack supplying unit, a centrifugal separation unit, a stopper opening unit, a dispensing unit, a stopper closing unit, a classification unit, and a sample storing unit, the sample treatment system further comprising shape detection means for detecting the shape of the stopper.

According to the present invention, the shape of a stopper of a stopper-equipped sample vessel can be successfully detected. Therefore, by enabling the use of two or more kinds of stopper-equipped sample vessels in the same sample treatment system, a wide choice of sample vessels is provided on the user side, and the flexibility as a sample treatment system is also increased.

DETAILED DESCRIPTION OF THE PREFERRED EMBODIMENTS

Embodiments of the present invention will be described with reference to FIG. 1 through FIG. 5.

Figure 1:
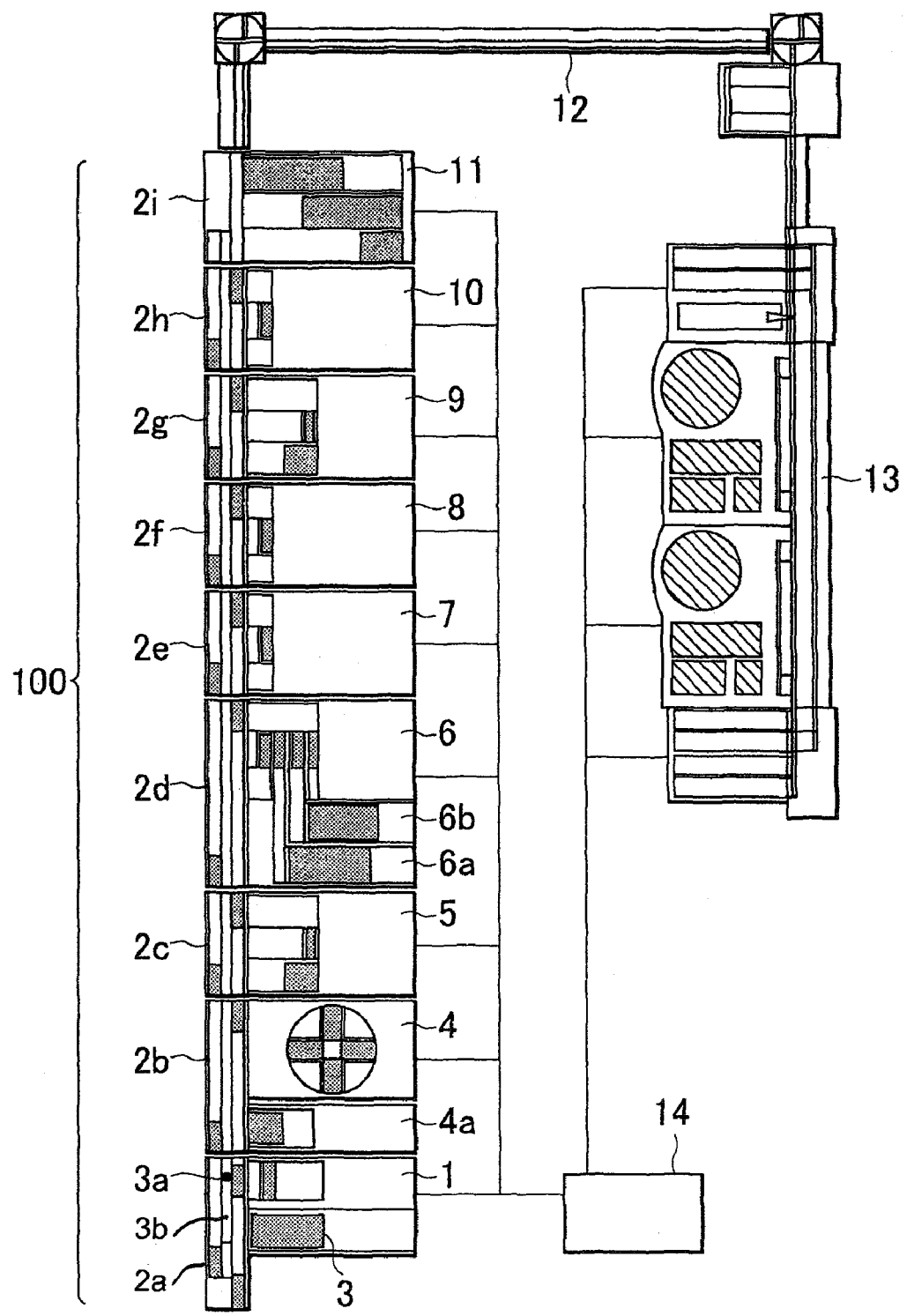
FIG. 1 is a diagram schematically illustrating the configuration of a sample treatment system according to an embodiment of the present invention.

First of all, an overall configuration of a sample treatment system according to an embodiment of the present invention will be described with reference to FIG. 1.

This sample treatment system includes:

a pretreatment unit 100 for pretreating a sample obtained from a patient; an analyzer 13 for analyzing a sample that has been pretreated; an analyzer connection line 12 for transferring, to the analyzer 13, the sample that has been pretreated by the pretreatment unit 100; and a control unit 14 for controlling and managing the pretreatment unit 100, the analyzer connection line 12, and the analyzer 13.

The pretreatment unit 100 includes: transfer lines 2a through 2i through which a sample rack 3 is transferred; and various kinds of treatment units that constitute the pretreatment unit 100. The various kinds of treatment units are lined up along the transfer lines 2a through 2i.

The pretreatment unit 100 further includes a sample rack supplying unit 1, a centrifugal separation unit 4, a stopper opening unit 5, an online dispensing unit 6, an offline dispensing unit 7, a bar code attaching unit 8, a stopper closing unit 9, a classification unit 10, and a sample storing unit 11.

The transfer line 2a is located along the sample rack supplying unit 1. The transfer line 2b is located along the centrifugal separation unit. The transfer line 2c is located along the stopper opening unit 5.

The transfer line 2d is located along the online dispensing unit 6. The transfer line 2e is located along the offline dispensing unit 7. The transfer line 2f is located along the bar code attaching unit 8.

The transfer line 2g is located along the stopper closing unit 9. The transfer line 2h is located along the classification unit 10. The transfer line 2i is located along the sample storing unit 11.

A sample obtained from a patient is put into a sample vessel. The sample vessel is placed in the sample rack 3; and the sample rack 3 containing the sample vessel is mounted on the sample rack supplying unit 1.

The sample rack 3, which has been supplied to a transfer line of the sample treatment system, is transferred from the sample rack providing unit 1 through the transfer lines 2a through 2i.

The transfer line 2a is provided with a detector 3a (shape detection means) for detecting the shape of a stopper included in the stopper-equipped sample vessel. It is possible to provide the transfer line 2a with vessel shape detection means for detecting a vessel shape of the stopper-equipped sample vessel.

In addition, it is also possible to provide the transfer line 2a with reading means 3b for reading out information including a bar code label that is attached to the sample vessel.

It is possible to locate the reading means 3b in an area in which the sample rack 3 of the sample rack supplying unit 1 is mounted (more specifically, in a sample rack storing space). It is also possible to locate the detector 3a (shape detection means) in the sample rack storing space.

The centrifugal separation unit 4 performs the centrifugal separation of each sample. The centrifugal separation unit 4 is equipped with a rack buffering unit 4a for keeping other sample racks 3 in a waiting sate during the centrifugal separation.

The stopper opening unit 5 opens the stopper of the sample vessel, which has been subjected to a centrifugal separation process.

The online dispensing unit 6 and the offline dispensing unit 7 dispense the sample that has been subjected to the centrifugal separation process. Samples of other sample vessels 6a, 6b are analyzed by the analyzer 13 that is connected through the analyzer connection line 12.

A sample vessel in the offline dispensing unit 7 is analyzed by an analyzer other than this sample treatment system.

The bar code attaching unit 8 attaches a bar code label, which is used to identify each sample, to a sample vessel (children sample) that has been subjected to dispensing by the offline dispensing unit 7 and the online dispensing unit 6.

After the dispensing, the stopper of the sample vessel is closed by the stopper closing unit 9. The classification unit 10 stores a sample vessel that has been subjected to the dispensing by the online dispensing unit 6, or passes the sample vessel to a subcontract, or the like. The sample storing unit 11 stores a rack that has already been handled.

The rack containing the sample vessel which has been subjected to the dispensing by the online dispensing unit 6 is transferred to the analyzer 13 that is connected through the analyzer connection line 12. The rack is then subjected to the analysis required for the rack in question.

Each of the treatment units 1 through 10 (including the transfer lines) of the pretreatment unit 100, and the analyzer 12, have a built-in process control function including a CPU. The process control function is connected to the control unit 14 through a communication cable through which information about various kinds of control is communicated. As a result, the operation of the sample treatment system is controlled.

Figure 2:
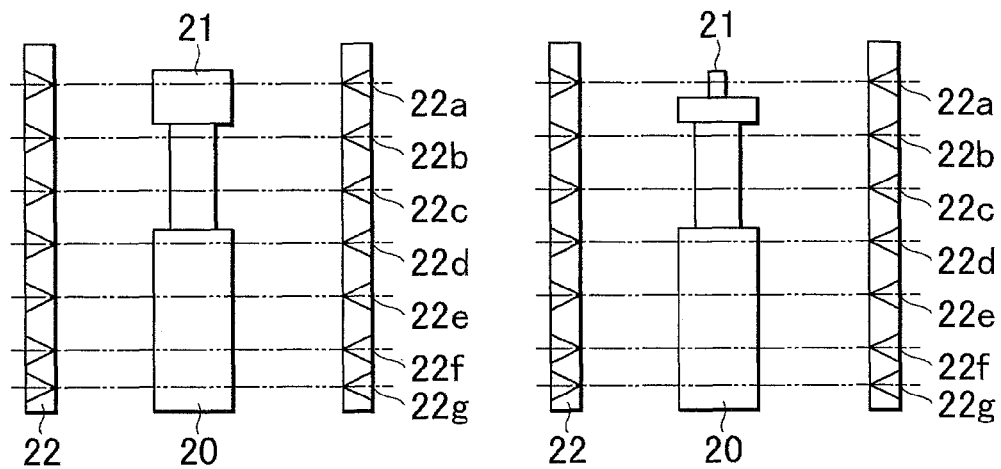
FIG. 2 is a diagram illustrating a detector for detecting the shape of a sample vessel, which is an example of a comparison with the embodiment of the present invention.

FIG. 2 is a side view illustrating a detector for detecting the shape of a sample vessel, which is an example of a comparison with an embodiment of the present invention.

The shape of a stopper-equipped sample vessel 21 placed in the sample rack 20 is detected by a plurality of sensors 22. The plurality of sensors 22, which are located in parallel with a length direction of the sample vessel, detect a height shape of the sample vessel on the basis of ON/OFF combinations of the individual sensors 22a through 22g.

However, it is difficult to reliably detect a stopper shape by this detection method. If the height of one sample vessel is the same as that of the other, even if their stopper shapes differ from each other as shown in FIGS. 2A, 2B, it is detected by mistake that the samples are the same. There is a risk that this false detection may cause a malfunction in the stopper opening unit, the pretreatment unit, or the like.

Figure 3:
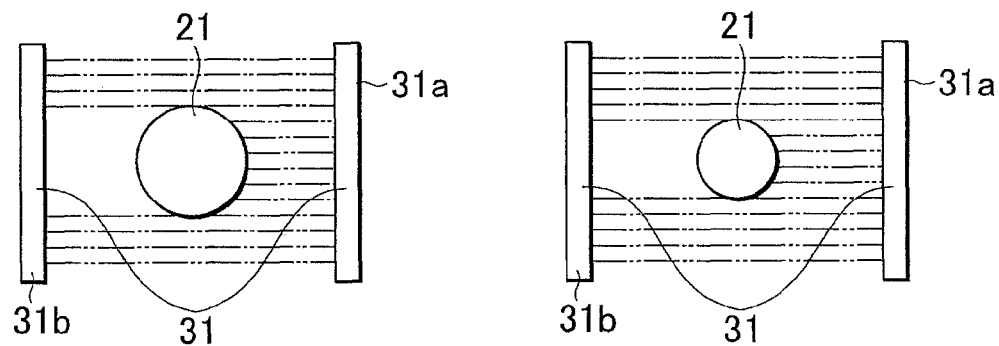
FIG. 3 is a plan view illustrating stopper shape detection means according to the embodiment of the present invention.
Figure 4:
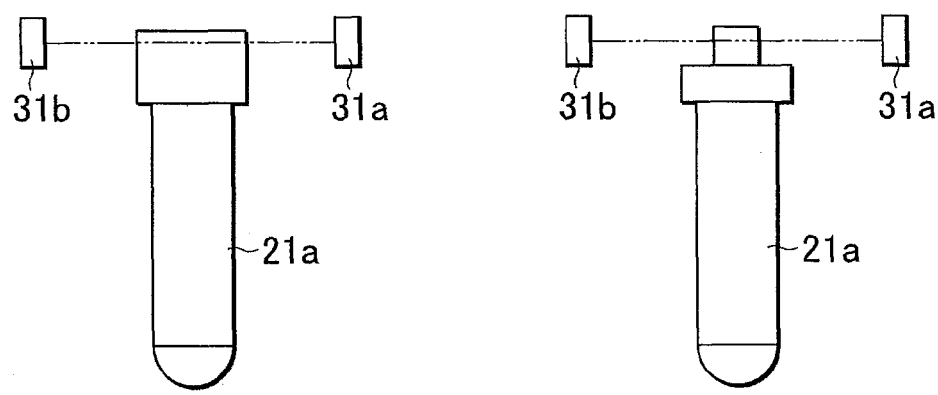
FIG. 4 is a side view illustrating stopper shape detection means according to the embodiment of the present invention.

FIGS. 3, 4 are diagrams each illustrating an example of shape detection means for detecting the shape of a stopper according to an embodiment of the present invention.

FIG. 3 is a plan view illustrating the detection. FIG. 4 is a side view illustrating the detection.

A photoelectric sensor 31 used as the shape detection means uses a fiber sensor. The photoelectric sensor 31 includes a light transmission unit 31a and a light receiving unit 31b. The light transmission unit 31a is constituted of a plurality of light emitting elements, whereas the light receiving unit 31b is constituted of a plurality of light receiving elements. The plurality of light emitting elements are lined up in a single row; and the plurality of light receiving elements are also lined up in a single row.

The photoelectric sensor 31 is located at such a position that the light transmission unit 31a and the light receiving unit 31b face each other with a stopper of the stopper-equipped sample vessel 21a or 21b being interposed therebetween. Further, the photoelectric sensor 31 is located in a manner that the light emitting elements constituting the light transmission unit 31a, and the light receiving elements constituting the light receiving unit 31b, are lined up in a diameter direction of the stopper.

Light beams emitted from the light transmission unit 31a are received by the light receiving unit 31b with some of the light beams missing, the missed light beams corresponding to a range of a diameter of the stopper. The shape of the stopper is identified in response to the missed light beams.

The photoelectric sensor 31 is provided with a predetermined threshold value of the amount of received light used to identify a shape. The shape of the stopper is identified according to the threshold value.

Lines shown in each of FIGS. 3A and 4A illustrate a state in which a stopper whose diameter is thick is detected. Lines shown in each of FIGS. 3B and 4B illustrate a state in which a stopper whose diameter is thin is detected. The shape of the stopper is identified by comparing the amount of light received by the light receiving unit 31b with the threshold value.

By providing a sliding mechanism that slides and moves the photoelectric sensor 31 in a longitudinal direction (length direction) of the stopper-equipped sample vessel, it is possible to measure the amount of received light over a range of the height of the stopper. Accordingly, it is possible to more correctly identify the shape of the stopper.

In addition, it is also possible to identify the shape of the sample vessel by measuring the amount of received light in a similar manner. If the shape of the sample vessel is identified by use of this shape detection means, it is possible to omit the vessel shape detection means described above.

Thus, by providing the shape detection means for detecting a stopper shape, it is possible to correctly and successfully detect the stopper shape of the stopper-equipped sample vessel. On the basis of information about the stopper shape that has been successfully detected, various kinds of treatment work to be executed in the pretreatment unit are smoothly executed without causing an error.

Figure 5:
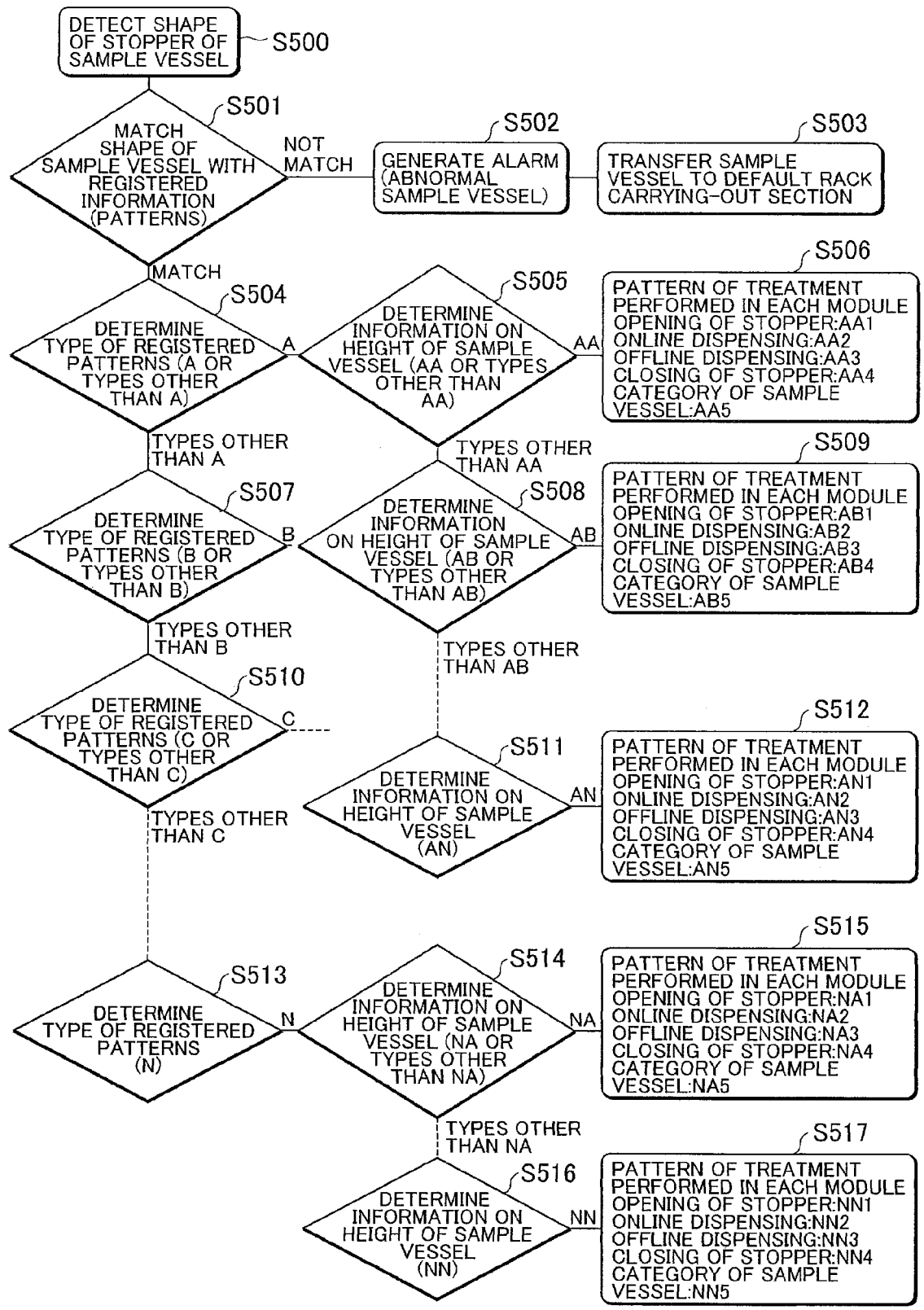
FIG. 5 is a flowchart illustrating the stopper shape judgment flow according to the embodiment of the present invention.

The stopper shape judgment flow will be described with reference to FIG. 5.

This is the flow of processing performed after the shape detection means identifies a stopper.

The shape of a stopper of a sample vessel is identified by the shape detection means as described above (step 500).

The identified shape of the stopper is collated with registered information that has been registered beforehand, and thereby a judgment is made as to whether or not the stopper whose shape has been identified has a stopper shape that can be handled at the time of treatment by the pretreatment unit (step S501). The collation is executed by use of the registered information stored in the storage unit of the control unit 14, and a collation function included in an operation processing unit of the control unit 14.

As a result of the collation, if it is judged that the identified shape of the stopper does not match the registered information, an alarm is generated in step S502, and the sample vessel in question is treated as an abnormal sample vessel. This abnormal stopper-equipped sample vessel is transferred to a default rack carrying-out section (step S503).

The abnormal stopper-equipped sample vessel, which has been judged to be "unmatched", is checked by an operator, and is subjected to, for example, redetection by the shape detection means.

If it is judged in the step S501 that the identified shape of the stopper matches the registered information, the process proceeds to a step S504. In the step S504, a type of a registered pattern is judged (A or other than A). If the type is judged to be A, the process proceeds to a step S505.

In the step S505, information about the height of the sample vessel is judged (AA or other than AA). If the information about the height of the sample vessel is judged to be AA, the process proceeds to a step S506. In the step S506, a treatment pattern of each pretreatment unit (each treatment module) is identified.

Treatment patterns identified in the step S506 include opening of stopper (AA1), online dispensing (AA2), offline dispensing (AA3), closing of stopper (AA4), and category of sample vessel (AA5).

After the above-described steps, judgment processing in steps S507 through S517 is also performed in a manner similar to that performed in the above-described steps. As a result, a treatment pattern of each pretreatment unit (each treatment module) is identified.

Thus, even if a stopper shape is identified by the detection of the shape detection means, a sample vessel whose stopper shape does not match the registered information is excluded. Only sample vessels with a stopper shape which match the registered information, and which match treatment conditions, exist in transfer lines and in the pretreatment unit. Therefore, treatment work smoothly progresses without delay.

In addition, as described above, sample vessels whose stopper shape matches the registered information are subjected to the treatment performed by the pretreatment unit. In addition, read information is acquired by reading out, by the reading means 3b, display information about the stopper-equipped sample vessel and the sample rack. This read information is also taken into consideration. Because corresponding sample vessels are transferred on the basis of the read information, it is possible to prevent a transfer error and a treatment error from occurring.

Moreover, stopper shape information included in the read information acquired by the reading means, and detection information acquired by the shape detection means, are subjected to the collation performed by a stopper shape judgment function included in the control unit 14 to determine whether or not they match each other. If it is judged to be "unmatched", higher priority is given to the detection information.

By giving higher priority to the detection information, it is possible to execute the stopper opening operation of the stopper opening unit without causing an error, for example, even if the stopper shape information included in the read information contains an error.

Furthermore, the stopper opening unit includes various kinds of stopper openers, each of which fits each stopper shape of the stopper-equipped sample vessels. Since the stopper opening unit performs the stopper opening operation by use of a stopper opener that suits the detection information acquired by the shape detection means, it is possible to reliably open a stopper without causing an error.

What is claimed is:

1. A sample treatment system comprising:
    a sample rack for supporting a stopper-equipped sample vessel in which collected samples are stored;
    a transfer line for transferring the sample rack;
    a pretreatment unit that is lined up along the transfer line, and that performs various kinds of pretreatment;
    a control unit for controlling the operation of the transfer line and the operation of the pretreatment unit; and
    shape detection means for detecting the shape of the stopper;
    wherein the pretreatment unit includes a sample rack supplying unit, a centrifugal separation unit, a stopper opening unit, a dispensing unit, a stopper closing unit, a classification unit, and a sample storing unit.

2. The sample treatment system according to claim 1,
    wherein said control unit stores registered information about stopper shapes that can be handled at the time of the treatment by the pretreatment unit, the registered information having been registered beforehand; and
    further comprising:
    a collation function of collating, with the registered information, detection information acquired as a result of the detection by the shape detection means so as to judge whether or not the detection information matches the registered information,
    wherein:
    a stopper-equipped sample vessel whose stopper shape is judged to be "unmatched" at the time of the collation is excluded from targets of the treatment.

3. The sample treatment system according to claim 2, further comprising:
    reading means for reading out information about the stopper-equipped sample vessel and the sample rack,
    wherein, the stopper-equipped sample vessel whose stopper shape is judged to be "matched" at the time of the collation is transferred to an appropriate unit on the basis of the detection information, and the read information read out by the reading means.

4. The sample treatment system according to claim 3, further comprising:
    a stopper shape judgment function of comparing stopper shape information included in the read information with the detection information to judge whether or not the stopper shape information matches the detection information,
    wherein if it is judged by the stopper shape judgment function that the stopper shape information does not match the detection information, then the stopper shape judgment function determines the stopper shape in accordance with the detection information.

5. The sample treatment system according to claim 1, wherein the stopper opening unit includes various kinds of stopper openers, each of which fits each stopper shape of stopper-equipped sample vessels; and a stopper opener is selected on the basis of the detection information acquired as a result of the detection by the shape detection means, before the stopper opener works.

6. The sample treatment system according to claim 1, wherein a photoelectric sensor including a fiber sensor is used as the shape detection means.

7. The sample treatment system according to claim 6, wherein the photoelectric sensor includes a light transmission unit including a plurality of light emitting elements, and a light receiving unit including a plurality of light receiving elements, and the photoelectric sensor is located at such a position that the light transmission unit and the light receiving unit face each other with the stopper being interposed therebetween, and the photoelectric sensor is also located in a manner that the light receiving elements included in the light receiving unit are lined up in a diameter direction of the stopper.

8. The sample treatment system according to claim 7, wherein the photoelectric sensor compares the amount of light received by the light receiving unit with a predetermined threshold value to identify a shape.

* * * * *